(12) United States Patent
Nord et al.

(10) Patent No.: US 6,517,552 B1
(45) Date of Patent: Feb. 11, 2003

(54) SUTURE RETRIEVER

(75) Inventors: Keith D. Nord, Jackson, TN (US); Robert M. Weber, Cheno Hills, CA (US); Stephen S. Burkhart, San Antonio, TX (US)

(73) Assignee: Arthrex, Inc., Naples, FL (US)

( * ) Notice: Subject to any disclaimer, the term of this patent is extended or adjusted under 35 U.S.C. 154(b) by 201 days.

(21) Appl. No.: 09/590,168

(22) Filed: Jun. 9, 2000

Related U.S. Application Data

(63) Continuation-in-part of application No. 09/178,416, filed on Oct. 28, 1998, now Pat. No. 6,074,403.
(60) Provisional application No. 60/063,444, filed on Oct. 29, 1997.

(51) Int. Cl.[7] ............................................. A61B 17/12
(52) U.S. Cl. ..................... 606/144; 606/139; 606/207
(58) Field of Search ................... 606/144, 147, 606/148, 222, 223, 205, 207; 112/116, 224

(56) References Cited

U.S. PATENT DOCUMENTS

| 5,222,977 | A | | 6/1993 | Esser |
| 5,234,443 | A | * | 8/1993 | Phan et al. .................. 606/144 |
| 5,405,354 | A | * | 4/1995 | Sarrett ......................... 606/148 |
| 5,499,991 | A | | 3/1996 | Garman et al. |
| 5,910,148 | A | * | 6/1999 | Reimels et al. ............. 606/144 |

OTHER PUBLICATIONS

René D. Esser, M.D., Arthroscopic Meniscus Repair: The Easy Way; The Journal of Arthroscopic and Related Surgery; pp. 231–233; vol. 9, No. 2, 1993.

* cited by examiner

Primary Examiner—David O. Reip
Assistant Examiner—Julian W. Woo
(74) Attorney, Agent, or Firm—Dickstein Shapiro Morin & Oshinsky, LLP

(57) ABSTRACT

An instrument for retrieving suture within a patient has a shaft with proximal and distal ends. The distal end terminates in a sharp tip. An opening is provided proximal to the sharp tip. A jaw captures suture slidably within the opening. A hand mechanism disposed on the proximal end of the shaft opens and closes the jaw.

19 Claims, 5 Drawing Sheets

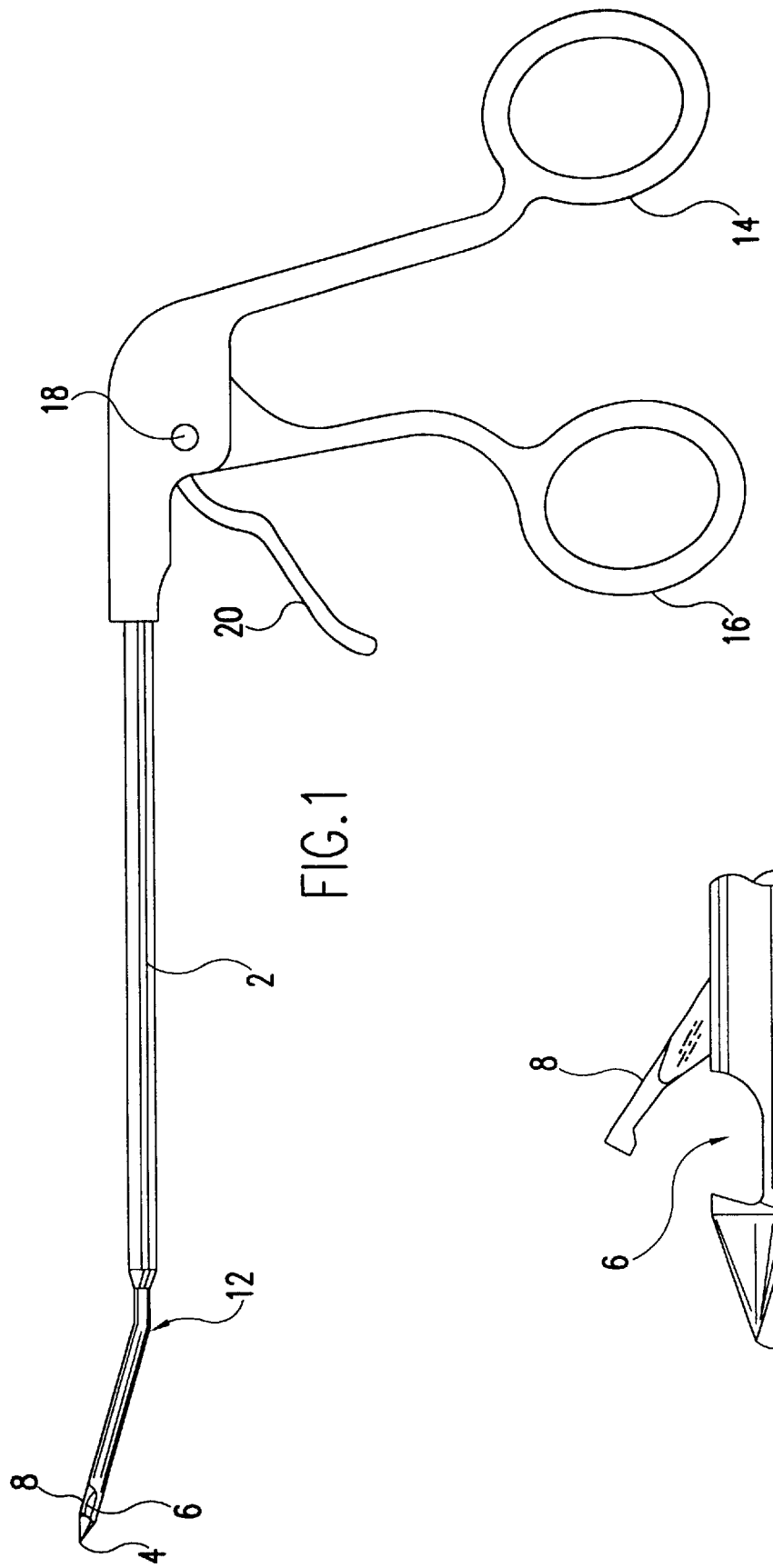
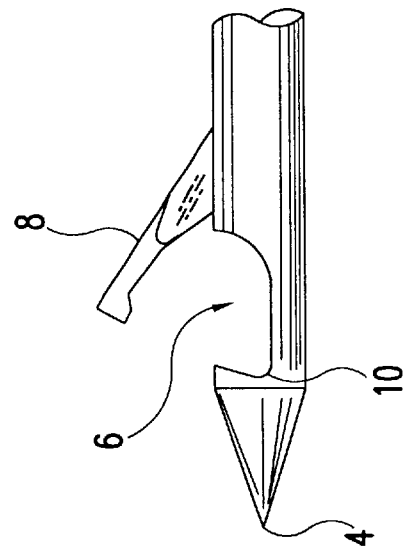

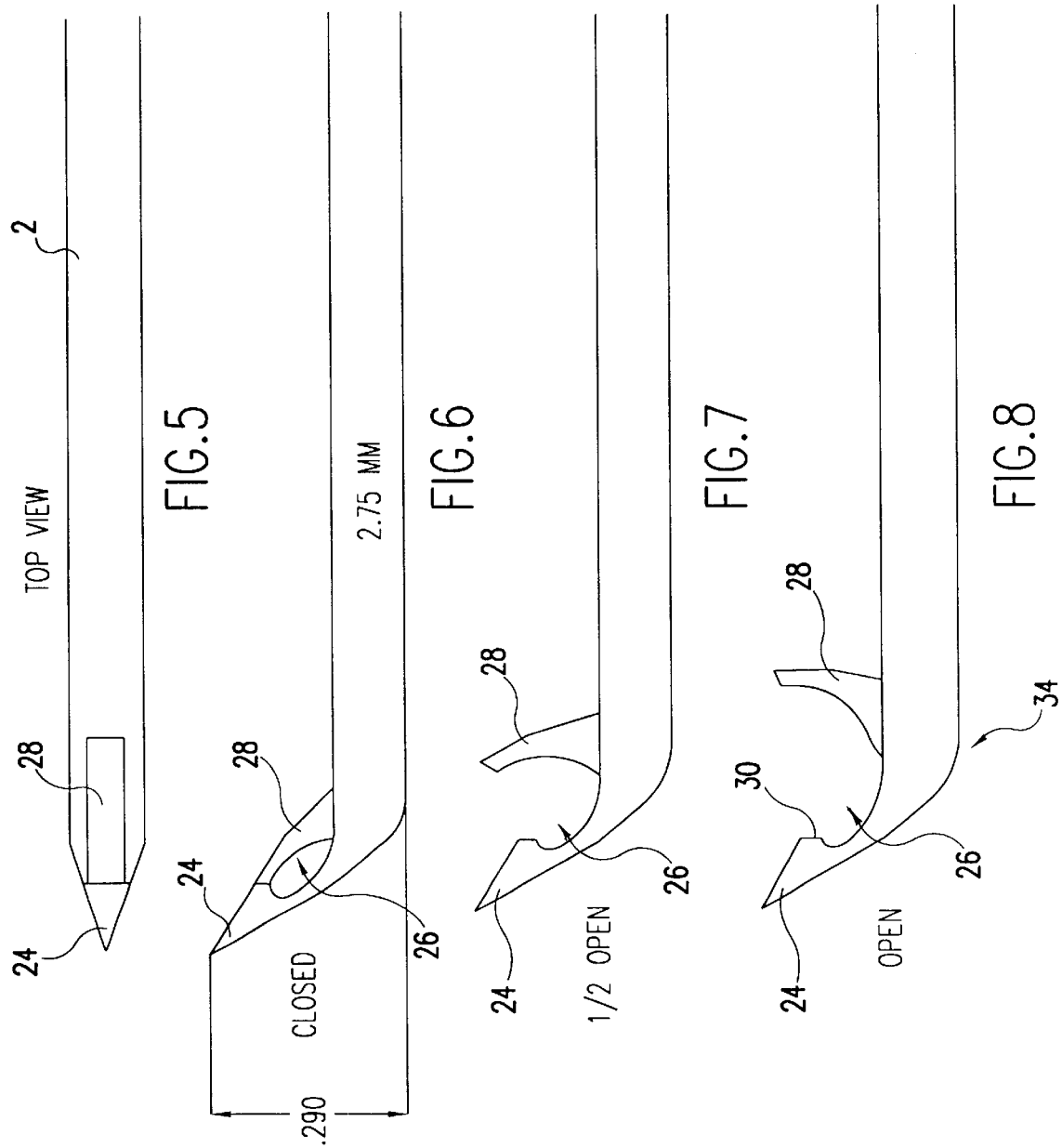

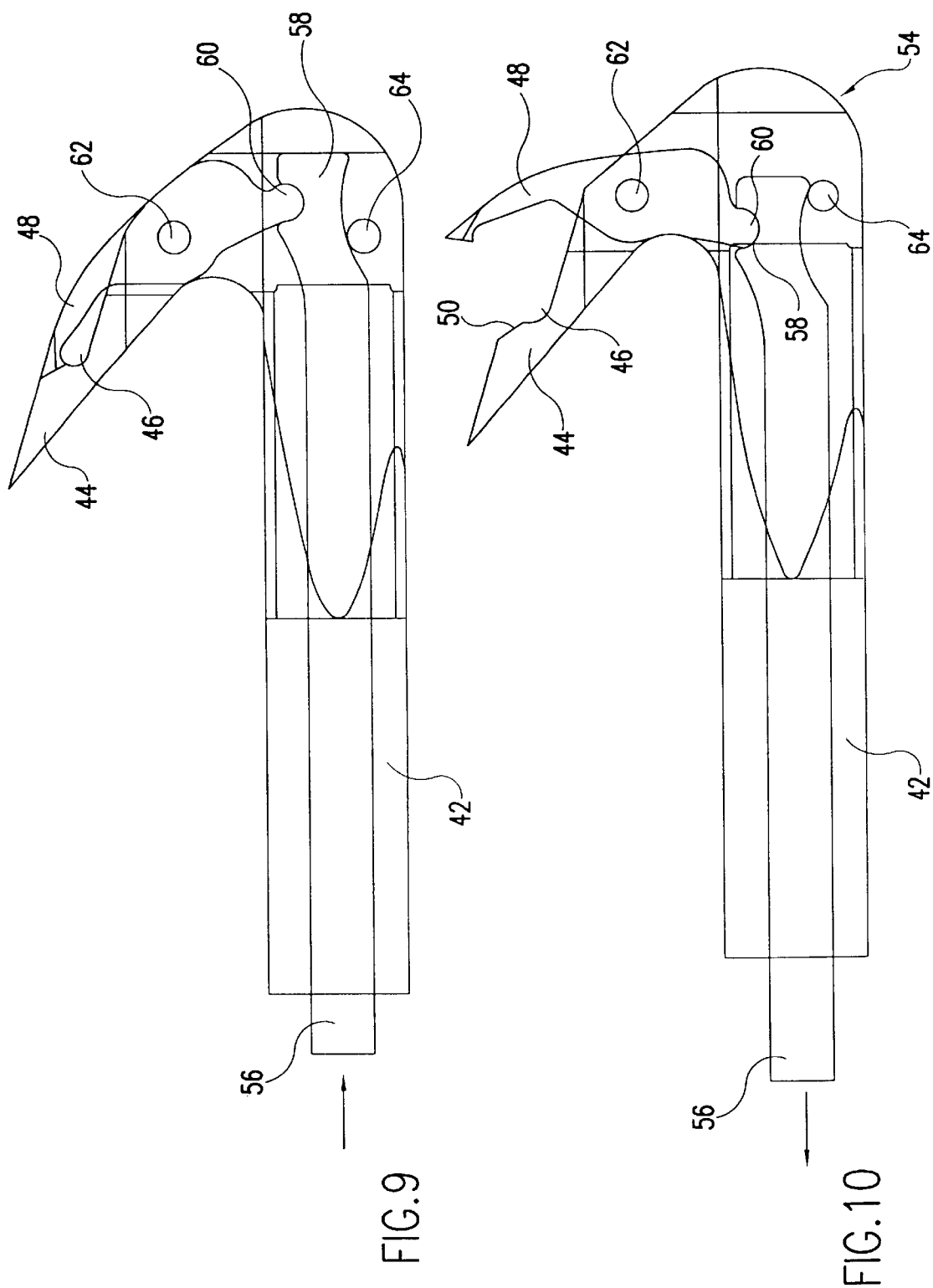

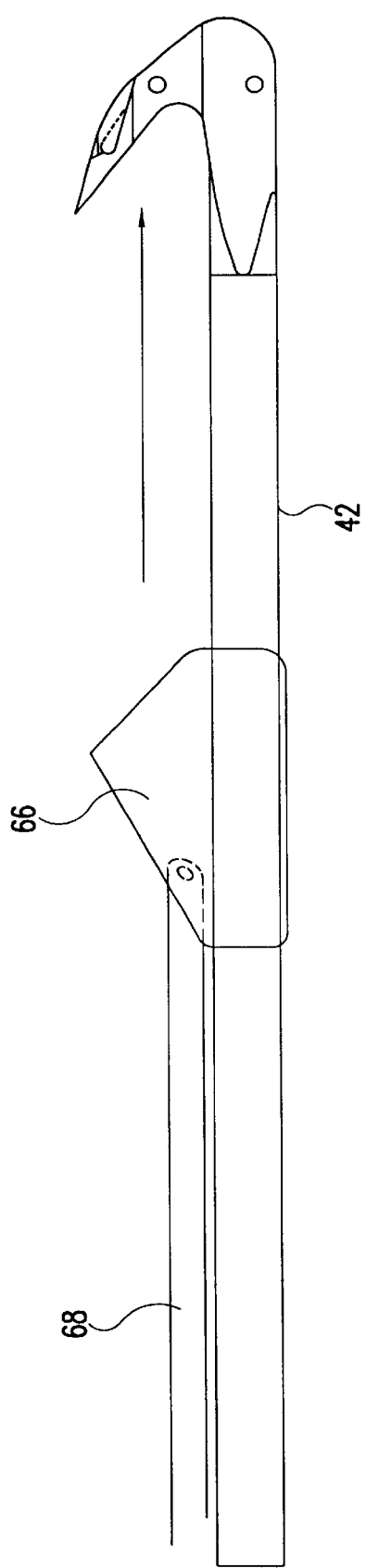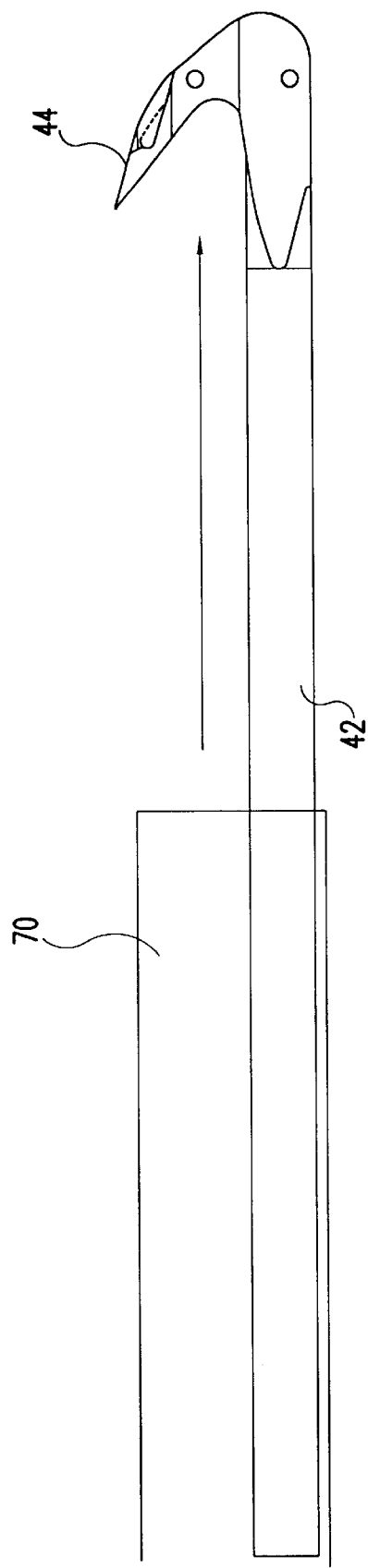

SUTURE RETRIEVER

This application is a continuation-in-part of application Ser. No. 09/178,416 filed on Oct. 28, 1998, now U.S. Pat. No. 6,074,403. This application claims the benefit of U.S. Provisional Application Serial No. 60/063,444, filed on Oct. 29, 1997, the disclosure of which is incorporated herein by reference.

BACKGROUND OF THE INVENTION

1. Field of the Invention

The present invention relates to endoscopic surgical methods and devices, and more specifically to methods and apparatus for manipulation of suture during endoscopic surgical procedures.

2. Description of the Related Art

Endoscopic suturing techniques and instruments have been developed in order to facilitate the suturing of tissue during endoscopic surgical procedures. The term "endoscopy" encompasses arthroscopy, laparoscopy, hysteroscopy, etc., and endoscopic surgery involves the performance of surgical procedures within a patient's body through small openings as opposed to conventional open surgery through large incisions. Access to a surgical work site within a patient's body is normally provided through one or more portals formed directly in the patient's body or through one or more cannulas inserted into the patient's body through small incisions. A chosen surgical procedure is carried out by a surgeon through the use of elongated instruments inserted through these cannulas and it often becomes necessary to suture selected tissue at the surgical work site.

Since the work site is only accessible through a small portal or cannula and since it is very difficult to tie sutures within the body, various devices and techniques have been developed to enable the surgeon to tie sutures endoscopically. For example, some procedures enable the surgeon to pass suture material through selected tissue, form a surgical knot extracorporeally and then move the knot with a knot pusher through the portal or cannula into position adjacent the desired tissue to be sutured. Some instruments used to pass the suture incorporate a hollow needle provided with some means, often a wire loop, to guide suture through the tissue pierced by the needle.

SUMMARY OF THE INVENTION

The present invention provides a hand instrument for retrieving suture within a patient. The suture retriever includes a shaft having a proximal end and a distal end. The distal end preferably terminates in a sharp tip. An opening in the shaft is disposed proximal to the distal end. A hinged jaw disposed on the shaft closes to capture suture within the opening in the shaft. A hand mechanism, preferably including finger loops, is disposed on the proximal end of the shaft for opening and closing the jaw.

Advantageously, the opening in the shaft is sized such that when the jaw is closed, suture captured within the opening by the jaw is allowed to slide freely as the suture grasper passes through soft tissue. Further, the opening preferably has a notched or sloped distal face, such that suture captured in the opening tends to slide more securely into the notch, away from the opening and the jaw.

For ease of use in various surgical situations, the instrument can be formed with a bend in the shaft, preferably proximal to the opening in the shaft. In particular for rotator cuff and glenoid labral repair, the shaft is bent upward at about a 15° angle, and the opening is disposed on an upper side of the shaft. Bends in other directions and of differing degrees can be provided, such as side bends of 15°, 30°, 45°, and 60°. A straight shafted instrument also can be provided according to the present invention.

The instrument is provided so as to pass through a 6 mm cannula, the jaw closing flush with the outer surface of the shaft. Advantageously, the shaft is tapered toward the distal end such that the distal tip has a 2.5 mm diameter for ease of penetrating soft tissue.

A method of endoscopically retrieving suture disposed within a patient using the instrument of the present invention includes closing the jaw using the hand mechanism and inserting the shaft of the instrument distally into the patient. The tissue to be sutured is penetrated with the sharp tip, and the jaw is opened. The opening in the shaft is positioned proximate a piece of suture disposed in the patient, and the jaw is closed to capture the suture within the opening. As the instrument is retrograded, the captured suture is pulled back through the tissue, the suture being allowed to slide freely through the closed opening to prevent damage to the suture.

Preferably, the jaw can be locked in the closed position. Accordingly, during instrument insertion for example, it is not necessary for the surgeon to maintain hand position at the finger loops of the instrument as the instrument is guided through tissue. Most preferably, a finger-actuated locking mechanism secures the hand mechanism in a closed, open, or any given operating position.

Other features and advantages of the present invention will become apparent from the following description of the invention which refers to the accompanying drawings.

BRIEF DESCRIPTION OF THE DRAWINGS

FIG. 1 is a side elevation of a suture retriever according to the present invention.

FIG. 2 is a detail of the distal tip of the suture retriever according to the present invention.

FIG. 5 is a partial plan view of the suture retriever of FIG. 3 shown in the closed position.

FIG. 6 is a partial elevation detailing the distal end of the suture retriever of FIG. 3 in the closed position.

FIG. 7 is a partial elevation detailing the distal end of the suture retriever of FIG. 3 in the half open position.

FIG. 8 is a partial elevation detailing the distal end of the suture retriever of FIG. 3 in the open position FIG. 9 is a detailed sectional view of the distal end of suture retriever according to a second alternative embodiment of the present invention, shown in the closed position.

FIG. 10 is a detailed sectional view of the distal end of the suture retriever of FIG. 9, shown in the open position.

FIG. 11 is a partial elevation of the suture retriever of FIG. 9, illustrating a point guard.

FIG. 12 is a partial elevation of the suture retriever of FIG. 9, illustrating an alternative point guard.

DETAILED DESCRIPTION OF THE PREFERRED EMBODIMENTS

Figure 3:
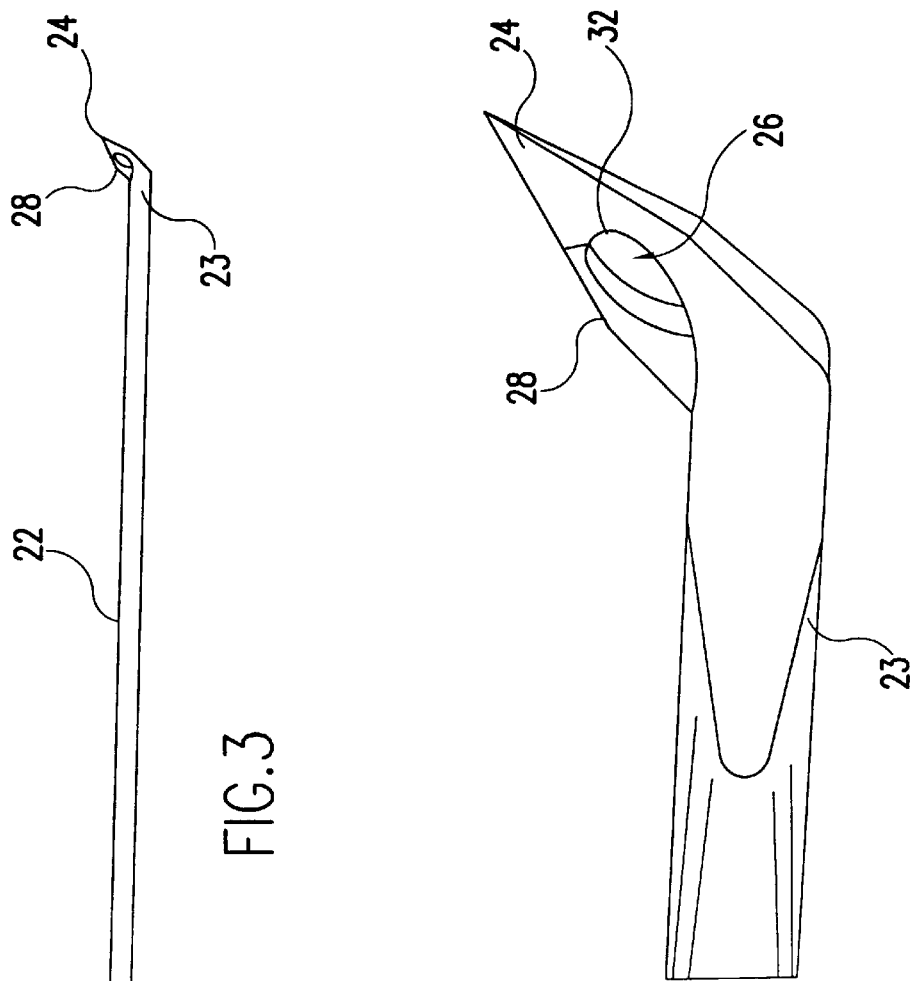
FIG. 3 is a perspective illustration of a suture retriever according to an alternative embodiment of the present invention.

Referring initially to FIG. 1, a suture retriever is shown according to a preferred embodiment of the present invention. The suture retriever includes a shaft 2 having a sharp distal tip 4. An opening 6 is formed in the shaft 2. A hinged jaw 8, shown in the closed position in FIG. 1, covers the opening 6.

In the closed position, the outer surface of jaw 8 forms a smooth surface contiguous with the outer surface of the shaft 2. A strand of suture captured in the opening, with the jaw closed, is free to slide within opening 6 as the suture retriever is pulled through soft tissue, thus protecting the suture from damage. The distal end of the jaw 8 mates with a groove (not shown) in the shaft 2 to provide a more stable closed position.

In the open position the jaw 8 provides access to the opening 6 for capturing suture, as shown in detail FIG. 2.

The opening 6 preferably has a notch 10 formed on the distal face of the opening, such that suture captured within the opening tends to slide more securely toward the bottom of the opening, rather than sliding up and out toward the jaw, as the instrument is pulled back through soft tissue.

Shaft 2 is provided with a 15° upward bend 12, according to a preferred embodiment of the present invention. The 15° upward bend positions the tip at the proper angle for passing through the glenoid labrum.

A hand mechanism is disposed on the proximal end of the shaft 2 by which the jaw 8 is operated. The hand mechanism includes a stationary thumb loop 14 and a moveable finger loop 16 secured by pivot 18. Moveable finger loop 16 actuates closing and opening of jaw 8 by way of a direct connection between the actuating mechanism and the jaw. Preferably, the direct connection is fully enclosed within shaft 2. A camlock mechanism operated by lever 20 locks the jaw in a closed position, for example, to facilitate insertion of the suture retriever through tissue.

The instrument preferably is designed to pass through a 6 mm cannula. The shaft 2 steps down from a maximum diameter of about 3.9 mm to a diameter of 2.5 mm near the sharp tip 4 for ease of penetration through tissue.

Figure 4:
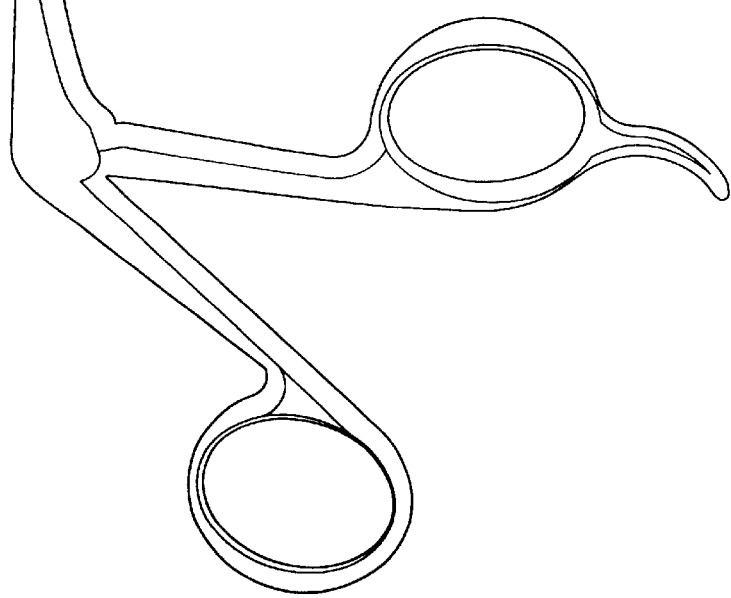
FIG. 4 is a partial perspective enlargement of the distal end of the suture retriever of FIG. 3.

Referring to FIGS. 3–8, an alternative embodiment of the present invention is shown in which the head of the instrument resembles a bird beak. The suture retriever includes a shaft in the form of a hollow tube 22. A machined head 23 extends from the distal end of the tube 22, terminating in a sharp distal tip 24. An opening 26 is covered by a hinged jaw 28.

In the closed position shown in FIGS. 3–6, the outer surface of jaw 28 forms a smooth surface contiguous with the outer surface of the distal tip 24, meeting the tip at bevel 30. A strand of suture captured in the opening, with the jaw closed, is free to slide within opening 26 as the suture retriever is pulled through soft tissue, thus protecting the suture from damage. In the open and half-open positions the jaw 28 provides access to the opening 26 for capturing suture, as shown in detail FIGS. 7 and 8.

The opening 26 preferably has a smooth, rounded notch 32 formed on the distal face of the opening, such that suture captured within the opening tends to slide more securely through the opening, remaining captured within the opening rather than sliding toward the jaw as the instrument is pulled back through soft tissue. In addition, or alternatively, the proximal end of the opening is rounded (not shown) to provide a smooth surface on which the suture can slide when using the instrument to pierce tissue and push suture through the pierced opening, as would be apparent to one of skill in the art.

The distal end of the instrument is provided with a 45° upward angle 34, according to a preferred embodiment of the present invention. Preferred options include straight, a 22° upward angle, and retrograde configurations as discussed in more detail below.

A hand mechanism disposed on the proximal end of the shaft is similar to that described above with respect to FIGS. 1 and 2, optionally without a locking mechanism as shown.

Referring to FIGS. 9–12, a second alternative embodiment of the present invention is shown. The suture retriever includes a shaft 42 having a sharp distal tip 44 directed proximally. An opening 46 is covered by a hinged jaw 48, shown in the closed position in FIG. 9, covers the opening 46.

In the closed position, the outer surface of jaw 48 forms a smooth surface contiguous with the outer surface of the distal tip 44, meeting the tip at bevel 50. A strand of suture captured in the opening, with the jaw closed, is free to slide within opening 46 as the suture retriever is pulled or pushed through soft tissue, thus protecting the suture from damage. In the open position the jaw 48 provides access to the opening 46 for capturing suture, as shown in FIG. 10.

The tip 44 angles back from shaft 42 to provide a 45° retrograde by way of upward angle 54, according to a preferred embodiment of the present invention. Optional configurations include a 90° upward angle.

A hand mechanism disposed on the proximal end of the shaft is similar to that described above with respect to FIGS. 1 and 2, above. The hand mechanism engages an actuating rod 56 contained within shaft 42, the proximal portion of which is formed as a hollow tube. The hand mechanism operates actuating rod 56 to close (FIG. 9) and open (FIG. 10) jaw 48.

More specifically, a slot 58 is formed at the distal end of actuating rod 56 which engages a tab 60. Jaw 48 pivots around pin 62. A second pin 64 provides a sliding surface for the distal end of rod 56 which has a relief formed in it to accommodate the pivoting motion of jaw 48. Accordingly, when the hand mechanism is operated to close jaw 48, actuating rod 56 moves in the direction of the arrow indicated in FIG. 9, whereby jaw 48 pivots in a counterclockwise direction around pin 62. Operating the hand mechanism to open jaw 48 causes the actuating rod to move in the direction of the arrow indicated in FIG. 10, thereby causing jaw 48 to pivot open in a clockwise direction. Other mechanisms would be obvious to one of skill in the art to change the back and forth movement of the actuating rod to the rotating or pivoting movement of the jaw, such as a rack and pinion, or pivot pin, for example.

Referring to FIG. 11, a point guard 66 for protecting the distal tip 44 is shown. Point guard 66 slides along shaft 42 and provides a covering over distal tip 44 to prevent the tip from damaging surrounding tissue as the instrument is being withdrawn from a surgical site, for example. A push rod 68 is actuated to advance and withdraw the point guard. An alternative point guard 70 is shown in FIG. 12. Point guard 70 is provided in the form of a tube that slides to cover distal tip 44.

Referred to above as a suture retriever, it is to be understood that the instruments of the present invention can be used to push loops of suture through tissue. Accordingly, a preferred method includes piercing tissue using the sharp distal tip of the instrument with the jaw in the closed position so that a length of suture slidably captured within the opening of the device is urged through the pierced hole in the tissue to form a loop. The instrument is retrograded with the jaw open to release the suture, leaving the loop of suture in place through the tissue and available to form a knot, for example.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. An instrument for retrieving or inserting suture within a patient, the instrument comprising:

a shaft having a proximal end and a distal end, the shaft having an opening disposed proximal to the distal end including a distal concave notch facing proximally for retaining captured suture within the opening as the instrument is drawn proximally;

a pivotably operable jaw for capturing suture within the opening, the jaw having a distal end disposed proximal to the distal end of the shaft when the jaw is in the closed position;

a hand mechanism disposed on the proximal end of the shaft for opening and closing the jaw; and an actuating rod disposed within the shaft and connecting between the hand mechanism and the jaw.

2. The instrument of claim 1, wherein the opening has a size such that when the jaw is closed, captured suture is allowed to slide freely within the opening.

3. The instrument of claim 1, wherein the shaft has a bend proximal to the opening in the shaft.

4. The instrument of claim 3, wherein the opening is disposed on an upper side of the shaft, and the shaft is bent upward.

5. The instrument of claim 4, wherein the shaft is bent upward at a 45° angle.

6. The instrument of claim 1, wherein the shaft is tapered toward the distal end.

7. The instrument of claim 1, wherein the jaw closes flush with an outer surface of the shaft.

8. The instrument of claim 1, wherein the hand mechanism includes a moveable finger loop and a stationary thumb loop.

9. The instrument of claim 1, further comprising a locking mechanism for maintaining the jaw in a fixed position.

10. The instrument of claim 1, further comprising a locking mechanism for maintaining the jaw in a closed position.

11. The instrument of claim 1, wherein the shaft comprises a hollow tube, and the actuating rod is contained within the shaft.

12. An instrument for retrieving or inserting suture within a patient, the instrument comprising:

a shaft having a proximal end and a distal end, the distal end having a retrograde tip angling proximally;

an opening disposed proximal to the distal end;

a pivotably operable jaw for capturing suture within the opening, the jaw having a distal end disposed proximal to the distal end of the shaft when the jaw is in the closed position;

a hand mechanism disposed on the proximal end of the shaft for opening and closing the jaw; and an actuating rod disposed within the shaft and connecting between the hand mechanism and the jaw.

13. The instrument of claim 12, wherein the opening in the shaft includes a notch on a proximal face of the opening for retaining captured suture within the opening.

14. The instrument of claim 12, further comprising a guard disposed on the shaft and movable into a position protecting the distal end.

15. The instrument of claim 14, wherein the guard is slidably movable along the shaft.

16. An instrument for retrieving or inserting suture within a patient, the instrument comprising:

a shaft having a proximal end and a distal end;

a pivotably operable jaw disposed on the distal end of the shaft, the jaw closing toward the shaft, the jaw and a distal portion of the shaft being configured such that an opening for capturing suture is formed between the jaw and the distal portion of the shaft when the jaw is closed, the jaw having a distal end disposed proximal to the distal end of the shaft when the jaw is in the closed position;

a hand mechanism disposed on the proximal end of the shaft when the jaw is in the closed position; and an actuating rod disposed within the shaft and connecting between the hand mechanism and the jaw.

17. The instrument of claim 16, wherein suture is captured slidably within the opening formed by the configuration of the jaw and the distal portion of the shaft when the jaw is closed.

18. The instrument of claim 16, wherein the opening is defined distally by a surface shaped so that suture captured within the opening slides toward a bottom of the opening as the instrument is drawn proximally.

19. The instrument of claim 16, wherein an outer surface of the jaw closes to form a surface contiguous with the outer surface of the shaft.

* * * * *